United States Patent [19]

Kalotay et al.

[11] 4,282,742

[45] Aug. 11, 1981

[54] DENSITOMETER

[75] Inventors: Paul Z. Kalotay, Monrovia; Iraj Ghahramani, Los Angeles, both of Calif.

[73] Assignee: International Telephone and Telegraph Corporation, New York, N.Y.

[21] Appl. No.: 837,454

[22] Filed: Sep. 28, 1977

[51] Int. Cl.³ .................................................. G01N 9/00
[52] U.S. Cl. .................................................. 73/32 A
[58] Field of Search .............................. 73/32 R, 32 A

[56] References Cited

U.S. PATENT DOCUMENTS

| | | | |
|---|---|---|---|
| 3,706,220 | 12/1972 | Miller | 73/32 A |
| 3,878,374 | 4/1975 | Schlatter | 73/32 A |
| 3,910,101 | 10/1975 | Kratky et al. | 73/32 A |
| 4,037,459 | 7/1977 | Schlatter | 73/32 A |

Primary Examiner—James J. Gill

[57] ABSTRACT

A vibration densitometer having a permanent magnet biased magnetostrictive drive unit, a maximum efficiency, and an automatic search for a resonant frequency signal.

1 Claim, 8 Drawing Figures

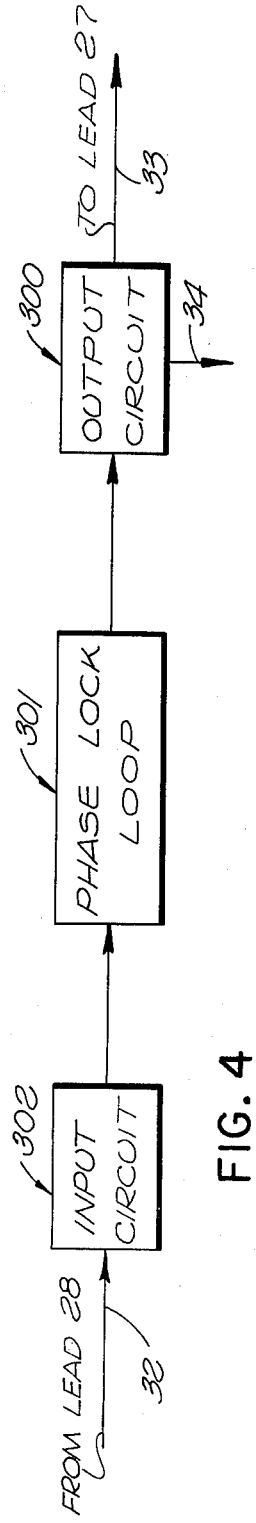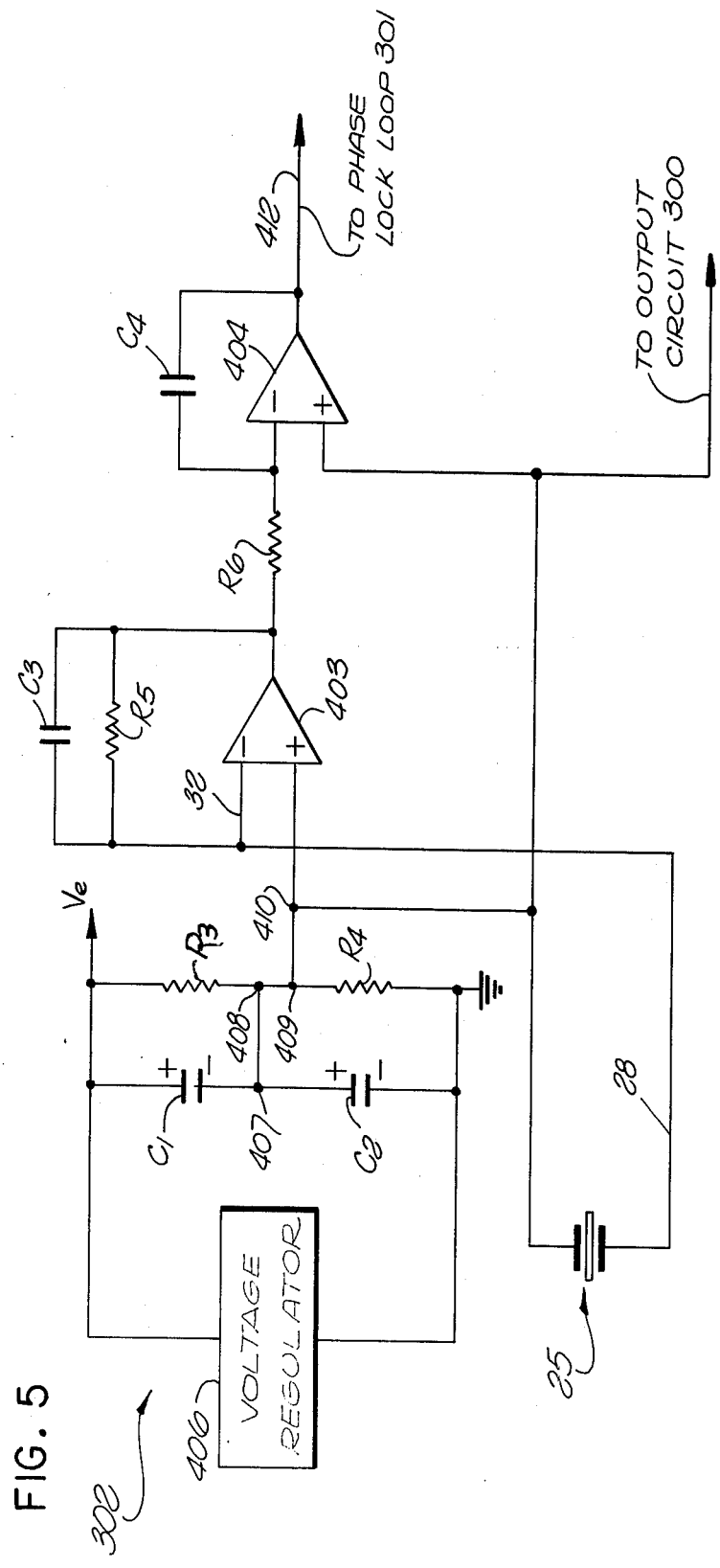

DENSITOMETER

BACKGROUND OF THE INVENTION

This invention relates to densitometers, and more particularly to a highly efficient vibration densitometer.

An efficient drive for a vibration densitometer is difficult to ascertain.

PRIOR ART STATEMENT

A loop circuit is disclosed in U.S. Pat. No. 3,795,136 issued Mar. 5, 1974; however, this loop circuit unfortunately utilizes a capacitor-crystal connection which is unnecessary and does not produce a differentiator in accordance with the present invention.

U.S. Pat. No. 3,878,374 issued Apr. 15, 1975, shows much of the structures disclosed herein except the efficient drive and the signal re-acquisition.

Copending application Ser. No. 729,779, filed Oct. 5, 1976, by M. H. NOVEMBER for DENSITOMETER was invented before the densitometer of this application and incorporates a permanent magnet drive. The said copending application was assigned to the assignee of this application.

For maximum energy transfer in theoretical forced vibration systems, see THEORY OF SOUND, LORD RAYLEIGH (Macmillan, London, 1894).

SUMMARY OF THE INVENTION

In accordance with the present invention a vibration densitometer is provided comprising: a probe including a vibratable member; electrical means actuable to impart vibration to said member; pick-up means to produce a first signal in synchronism with said member vibration; a loop circuit connected from said pick-up means to said electrical means to form an electromechanical oscillator, said loop circuit producing an output signal which is of a phase such that when it is impressed upon said electrical means, said electrical means applies an alternating force to said member of a phase leading that of said member by 90 degrees; and means connected from said loop circuit to produce a utility signal which is a known function of the density of a fluid in which said member is immersed.

Another embodiment of the present invention includes a vibration densitometer comprising: a probe including a vibratable member; electrical means actuable to impart vibration to said member; pick-up means to produce a first signal in synchronism with said member vibration; a loop circuit connected from said pick-up means to said electrical means to form an electromechanical oscillator; means connected from said loop circuit to produce a utility signal which is a known function of the density of the fluid in which said member is immersed, said loop circuit including a phase lock loop, said phase lock loop including a phase detector having first and second inputs, an output, a voltage controlled oscillator (VCO) having an input and an output, a resistor connected from said phase detector output to said VCO input, a capacitor connected from said VCO input to ground, a unijunction transistor having a gate connected from said VCO input, said VCO output being connected to said phase detector second input; an input circuit connected from said pick-up means to said phase detector first input; and an output circuit connected from said VCO output to said electrical means.

The above-described and other advantages of the present invention will be better understood from the following detailed description when considered in connection with the accompanying drawings.

BRIEF DESCRIPTION OF THE DRAWINGS

In the drawings, which are to be regarded as merely illustrative:

FIG. 4 is a block diagram of a loop circuit shown in FIG. 1 and constructed in accordance with the present invention;

FIG. 5 is a schematic diagram of an input circuit shown in FIG. 4;

DESCRIPTION OF THE PREFERRED EMBODIMENT

Figure 1:
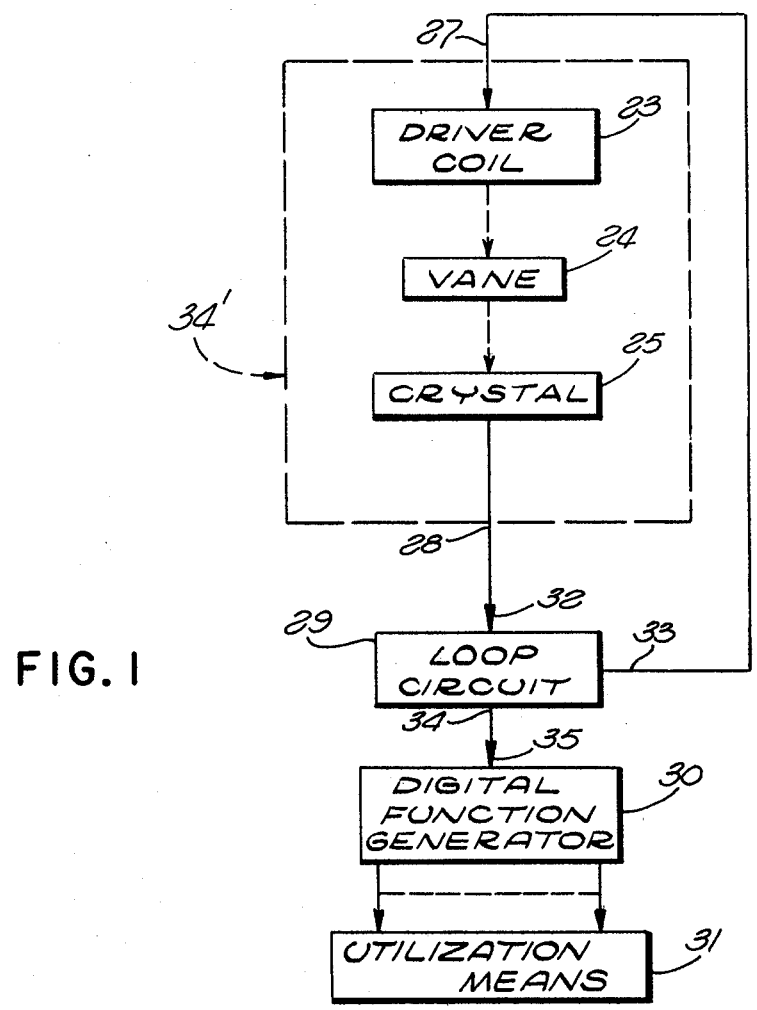
FIG. 1 is a block diagram of a densitometer constructed in accordance with the present invention.
Figure 3:
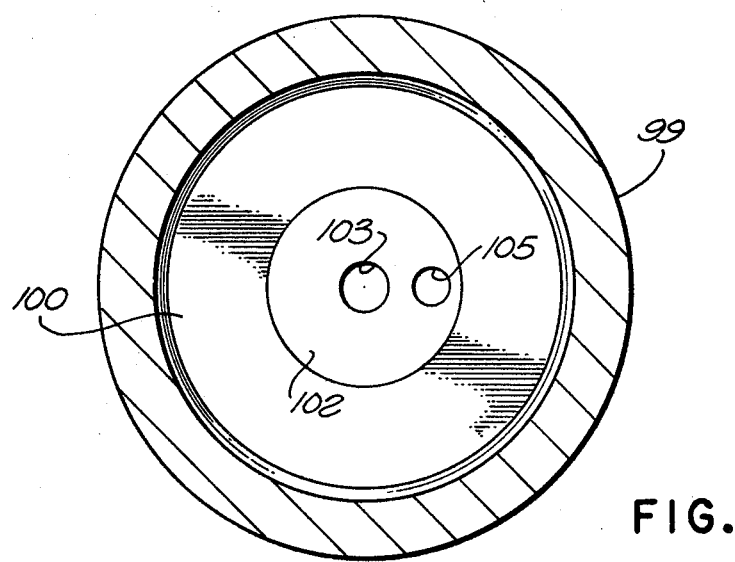
FIG. 3 is a transverse sectional view taken on the line 3—3 shown in FIG. 2.

In the drawings, in FIG. 1, a vibration densitometer probe is indicated at 34' having a driver coil 23, a vane 24 and a piezoelectric crystal 25.

Probe 34' has an input lead 27 and an output lead 28.

Other blocks shown in FIG. 1 are a loop circuit 29, a digital function generator 30 and utilization means 31. Loop circuit 29 has an input lead 32 and output leads 33 and 34. Digital function generator 30 has an input lead 35 connected from loop circuit output lead 34. The output of digital function generator 30 is connected to utilization means 31.

The output lead 28 of probe 34' is connected to the input lead 32 of loop circuit 29. The input lead 27 of probe 34' is connected from the output lead 33 of loop circuit 29. Probe 34' and loop circuit 29 form a closed loop electromechanical oscillator. Vane 24 is submerged in a fluid. The density of the fluid is a function of the frequency at which vane 24 vibrates. For the theory of operation, see U.S. Pat. Nos. 3,878,374 and 3,958,446 issued Apr. 15, 1975, and May 25, 1976, respectively.

Digital function generator 30 may have its input lead 35 connected from lead 33 or at other points in loop circuit 29. Loop circuit 29 impresses a square wave voltage on input lead 35 of digital function generator 30.

Utilization means 31 shown in FIG. 1 may be a density indicator, a specific gravity indicator, a process controller or otherwise.

The following patents are hereby incorporated herein by this reference hereto:

U.S. Pat. No. 3,677,067.
U.S. Pat. No. 3,706,220.
U.S. Pat. No. 3,738,155.
U.S. Pat. No. 3,741,000.
U.S. Pat. No. 3,878,374.
U.S. Pat. No. 3,958,446.

Probe 34' shown in FIG. 1 may be entirely conventional except as noted hereinafter and because it incorporates no preamplifier between crystal 25 and loop circuit 29. Probe 34' may, for example, be similar to those shown and/or described in the above-listed patents.

OPERATION

In the embodiment of the invention shown in FIG. 1, probe 34' and loop circuit 29 provide an electromechanical oscillator which oscillates at a frequency dependent upon the density of the fluid in which vane 24 is immersed. The same is true of the pulse repetition frequency of a square wave voltage applied to the input lead 35 of digital function generator 30.

Digital function generator 30 may be described as a digital linearization circuit. It produces a digital output directly proportional to density from the input signal thereto impressed upon the input lead 35 thereto.

Figure 2:
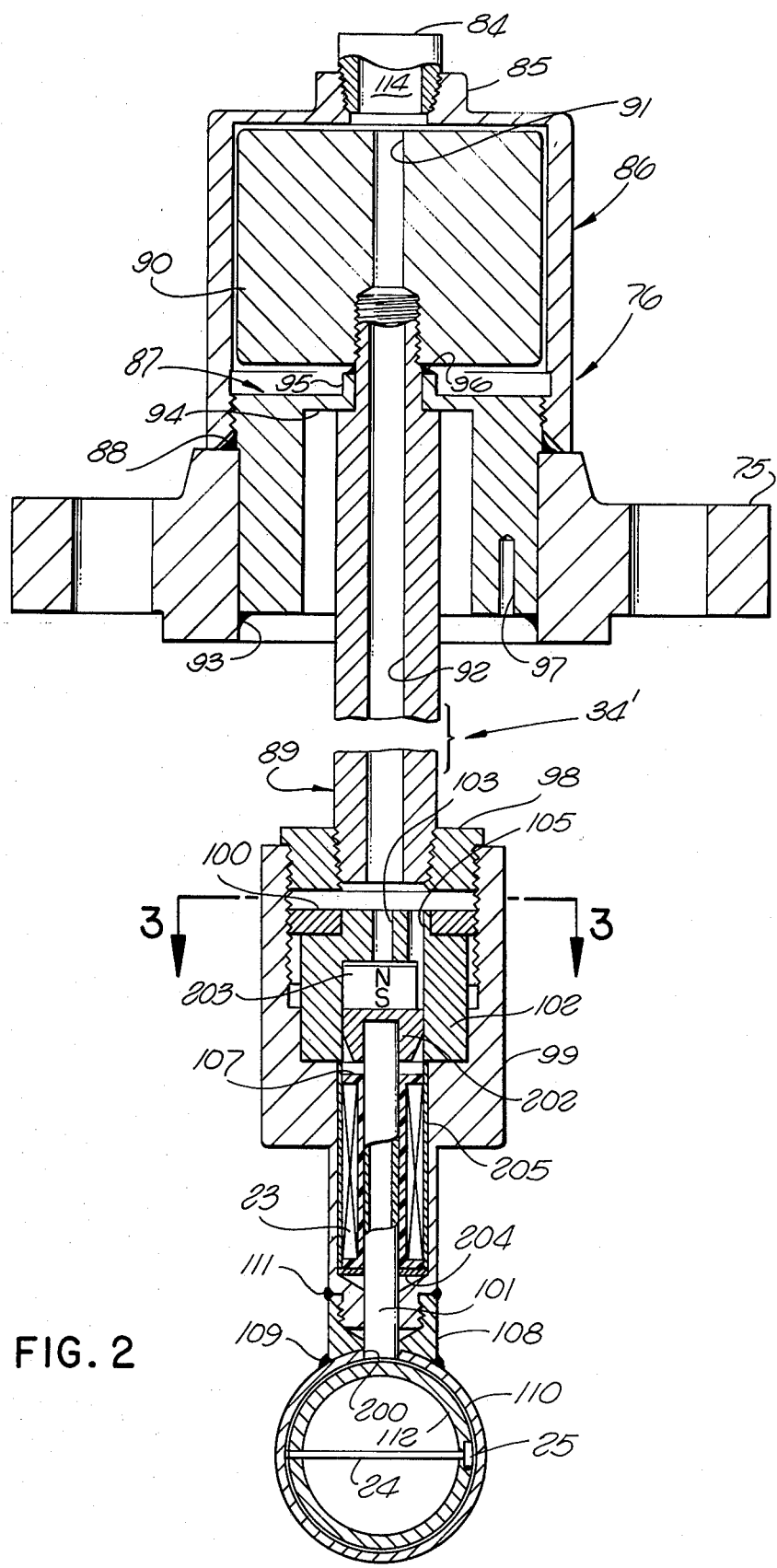
FIG. 2 is a vertical sectional view through the densitometer probe.

The manner in which probe 34' of FIG. 2 fits into a pipeline is explained in U.S. Pat. No. 3,958,446.

A vertical sectional view of probe 34' is shown in FIG. 2 where assembly 76 includes a nipple 84 threaded into a hollow cylindrical projection 85 of an end cap 86. End cap 86 is threaded to a body 87. Flange 75, end cap 86 and body 87 are welded or soldered together at 88. A hollow shaft 89 is externally threaded into a cylinder 90 that is solid except for a hole 91 which extends completely therethrough and is in communication with the hollow interior of shaft 89. Body 87 is welded at 93 to flange 75, and is provided with a thin web 94 which has an upwardly extending cylindrical projection 95 that is welded at 96 to shaft 89 and to cylinder 90. Body 87 may be provided with a pin hole 97, if desired, so that it may be held while end cap 86 is turned or threaded thereto.

Shaft 89 is, in turn, fixed to a ferrule 98 by being threaded thereinto. Ferrule 98, in turn, is fixed to a body 99 by being threaded thereinto.

A ring 100 is threaded into body 99. A magnetostrictive tube 101 which is hollow and open at both ends is slidable in a hole 200 through a cylinder 110 and press fit into a soft iron plug 202 that is, in turn, press fit into a body 102. A permanent magnet 203 is fixed in body 102. Body 102 may have holes 103 and 105 to below plug 202. See U.S. Pat No. 3,958,446. Driver coil 23 is shown again in FIG. 2 on a dielectric spool 107 press fit onto tube 101. A ferrule 108 is welded at 109 to cylinder 110. Body 99 is threaded into ferrule 108 and welded thereto at 111. Tube 101 bears against the external cylindrical surface of a cylinder 112. Vane 24 is fixed inside cylinder 110 in a manner identical to that illustrated, in one or more of several patents including but not limited to U.S. Pat. No. 3,677,067. The same is true of crystal 25.

Cylinders 110 and 112, vane 24, and crystal 25 may be identical to those disclosed in the last mentioned patent, if desired. Tube 101 is slidable through the lower end of body 99 and is slidable through the circular holes in ferrule 108 and cylinder 110.

A ferromagnetic washer is provided at 204. A ferromagnetic cylinder is provided at 205.

A more detailed explanation of the operation of a vibration densitometer employing the structure disclosed herein is set forth in all the patents cited herein.

Magnet 203 is constructed so as to cause vane 24 to be vibrated at the output frequency of crystal 25. In FIG. 1, lead 33 may or may not carry a signal having a component of D.C. voltage or current, or only A.C.

Magnet 203 may be poled as shown or poled in the opposite direction.

The invention as shown in FIG. 1 may be somewhat conventional as shown in the patents and/or application cited hereinbefore except for the said preamplifier omission, and except for loop circuit 29. Loop circuit 29 is new according to the present invention.

Loop circuit 29 is shown in FIG. 4 including an input circuit 302, a phase lock loop 301, and an output circuit 300 connected in succession in that order from lead 28 to lead 27.

Figure 7:
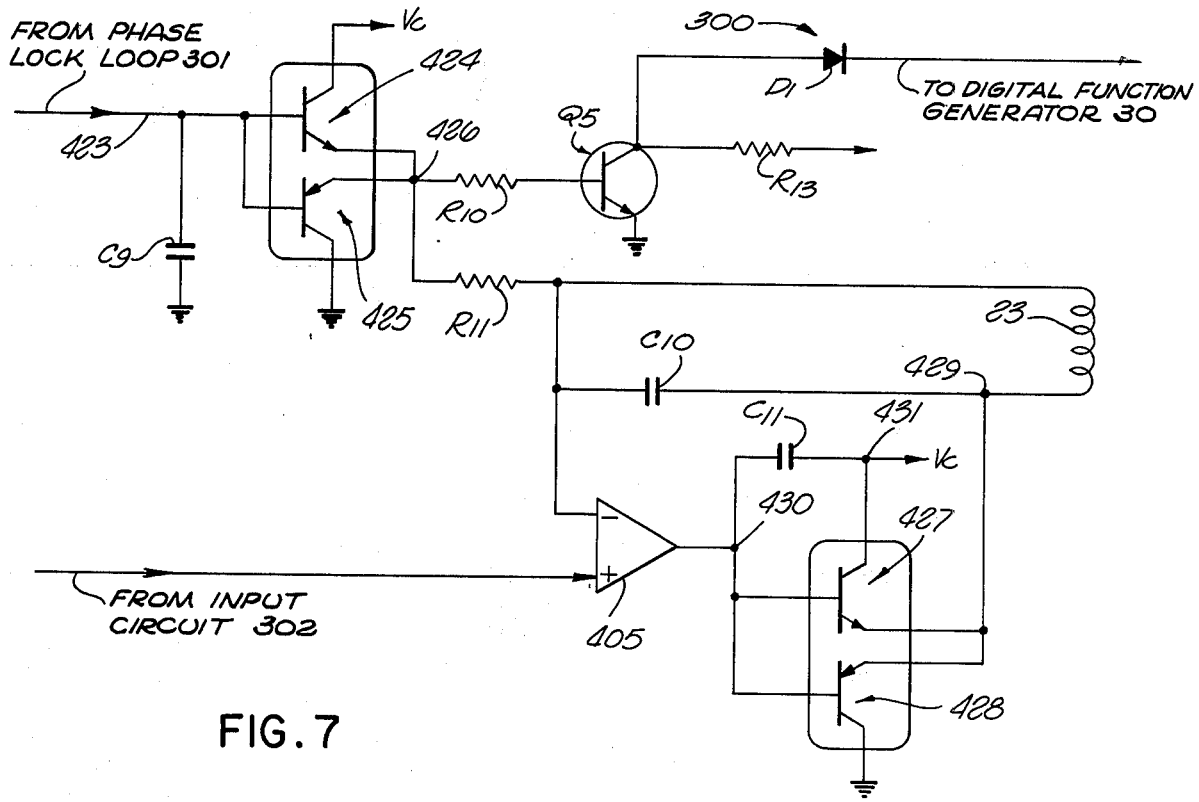
FIG. 7 is a schematic diagram of an output circuit shown in FIG. 4.

One side of crystal 25 is connected to each of the noninverting inputs of three differential amplifiers 403, 404 and 405 (see FIGS. 5 and 7).

The other side of crystal 25 is connected to the inverting input of amplifier 403. Amplifier 403 has a feedback resistor R5 which makes the circuit a differentiator because crystal 25 is equivalent to an alternator and a capacitor in series. The current in coil 23 (FIGS. 1 and 7) thus has a phase which leads the crystal voltage by about 90 degrees for maximum drive efficiency. For some prior art on the subject of forced vibrations, see the said RAYLEIGH reference.

In FIG. 5, a voltage regulator 406 is connected from potential $V_e$ to ground.

Capacitors C1 and C2 are connected in succession from $V_e$ to ground. The same is true of resistors R3 and R4. Junctions 407, 408, 409 and 410 are connected together.

A capacitor C3 in parallel with resistor R5 provides a rather flat gain over the frequency band of interest.

Without substantially changing the phase of the output signal of amplifier 403, resistor R6, capacitor C4 and amplifier 404 form a conventional integrator to suppress high frequencies outside of the band of interest.

Figure 6:
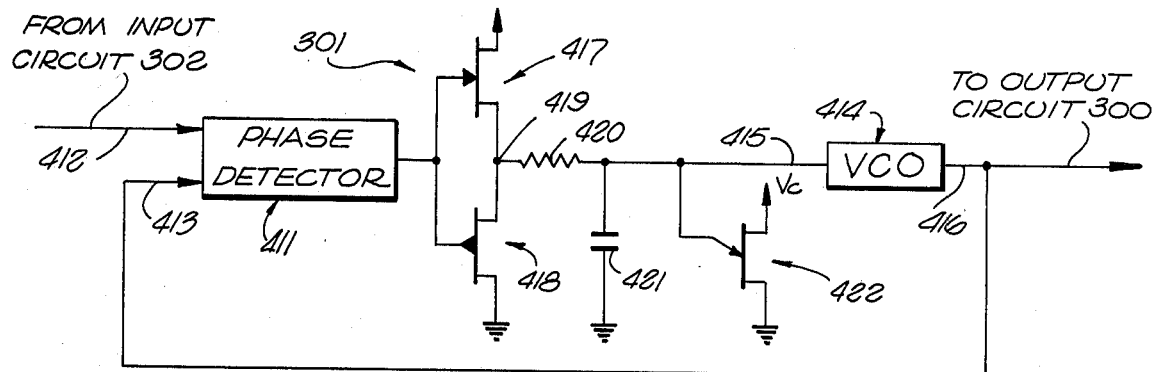
FIG. 6 is a schematic diagram of a phase lock loop shown in FIG. 4.

The phase lock loop 301 of FIG. 6 includes a phase detector 411 having first and second input leads 412 and 413, respectively. See the connection of lead 412 in FIG. 5.

A voltage controlled oscillator (VCO) 414 is also provided having an input lead 415, and an output lead 416 connected to phase detector input lead 413.

At 417 and 418 there are respectively provided conventional p-type and n-type complimentary metal oxide silicon insulated gate field effect transistors (CMOS). Junction 419 is maintained at $V_c$ or at ground, or there is an open circuit from junction 419 to resistor 420.

When junction 419 is at $V_c$, capacitor 421 charges toward the tracking voltage and VCO 414 tracks the input on lead 412. Should vane 24 be subjected to a shock, capacitor 421 will continue to charge up until unijunction transistor 422 fires. Capacitor 421 will then discharge and begin to charge up again to the tracking voltage.

In FIG. 7 a lead 423 is connected from VCO output lead 416 (FIG. 6). A capacitor C9 is connected from lead 423 to ground. Transistors 424 and 425 are connected from lead 423 to an output junction 426. Resistor R10, transistor Q5, resistor R13, and diode D1 form an amplifier with a rectified output.

A resistor R11 is connected from junction 426 to the inverting input of amplifier 405. The noninverting input is connected from input circuit 302.

Transistors 427 and 428 are connected from the output of amplifier 405 to a junction 429. Junctions are provided at 430 and 431. The output of amplifier 405 is connected to junction 430. A capacitor C11 is connected between junctions 430 and 431. Coil 23 and capacitor C10 are connected in parallel from junction 429 to the inverting input of amplifier 405.

Figure 8:
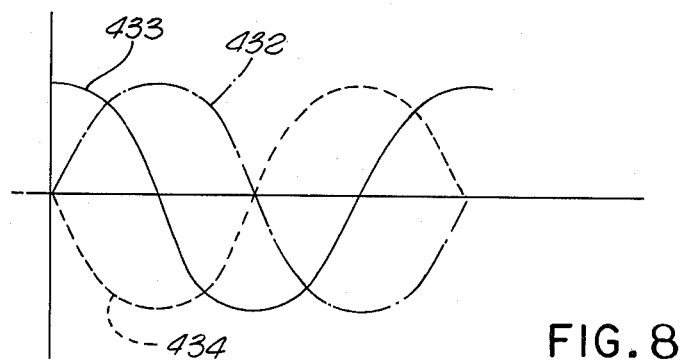
FIG. 8 is a graph of a group of waveforms characteristic of the operation of the system of FIG. 1.

In FIG. 8, vane 24 may vibrate as at 432. The current flowing in coil 23 or the fundamental of any square wave or other periodic current passing therethrough may be as shown at 433 leading 432 by 90 degrees. The output voltage of crystal 25 may be 432 or 434. The current in coil 25 should be effectively 90 degrees out of phase with 432 or 434, whichever gives maximum efficiency.

The signals, by phase, may be briefly traced through the feedback path illustrated in FIGS. 5-7 in the following summary.

In FIG. 5, the signal leaves crystal 25 via lead 28 through amplifiers 403 and 404 without substantial change in phase.

There is no substantial phase change in FIG. 6 because VCO 414 is always driven in a manner such that signals on leads 412 and 413 are in phase as is conventional with a phase lock loop.

There is no substantial phase shift in FIG. 7. Further, it is conventional to drive a load (e.g. coil 23) with an amplifier (e.g. 405) with feedback from the load. In this case, the inverting input lead of the amplifier 405 is maintained at a constant potential (in this instance at the potential of junction 410 in FIG. 5). The input impedances of both inverting and noninverting inputs of amplifier 405 is essentially infinite or very large as is well known. This, therefore, means that the current through resistor R11 is equal to the current through driver coil 23. A voltage-to-current conversion is thus made. Note that the desired signal is a voltage which appears at junction 426.

It is desired that the current through driver coil 23 be controlled because it is the current therethrough that determines the force on vane 24. The drive is magnetostrictive and thus relies on electromagnetism. See magnetostrictive tube 101 in FIG. 2. Only a current produces electromagnetism (not a voltage).

For a more detailed description of how the voltage input to amplifier 405 is transformed into a current proportional to the input voltage, which current is conducted through driver coil 23, see U.S. Pat. No. 3,757,234.

What is claimed is:

1. A vibration densitometer comprising: a probe including a vibratable member; electrical means actuable to impart vibration to said member; pick-up means to produce a first signal in synchronism with said member vibration; a loop circuit connected from said pick-up means to said electrical means to form an electromechanical oscillator; means connected from said loop circuit to produce a utility signal which is a known function of the density of the fluid in which said member is immersed, said loop circuit including a phase lock loop, said phase lock loop including a phase detector having first and second inputs, an output, a voltage controlled oscillator (VCO) having an input and an output, a resistor connected from said phase detector output to said VCO input, a capacitor connected from said VCO input to ground, a unijunction transistor having a gate connected from said VCO input, said VCO output being connected to said phase detector second input; an input circuit connected from said pick-up means to said phase detector first input; and an output circuit connected from said VCO output to said electrical means.

* * * * *